(12) United States Patent
Duquet et al.

(10) Patent No.: US 10,194,729 B2
(45) Date of Patent: Feb. 5, 2019

(54) ASSEMBLY FOR DISPENSING AND APPLYING A FLUID PRODUCT

(71) Applicant: APTAR FRANCE SAS, Le Neubourg (FR)

(72) Inventors: Frederic Duquet, Crespieres (FR); Christophe Pierre, Saint Sebastien de Morsent (FR)

(73) Assignee: APTAR FRANCE SAS, Le Neubourg (FR)

( * ) Notice: Subject to any disclaimer, the term of this patent is extended or adjusted under 35 U.S.C. 154(b) by 266 days.

(21) Appl. No.: 15/308,889

(22) PCT Filed: May 5, 2015

(86) PCT No.: PCT/FR2015/051185
§ 371 (c)(1),
(2) Date: Nov. 4, 2016

(87) PCT Pub. No.: WO2015/170048
PCT Pub. Date: Nov. 12, 2015

(65) Prior Publication Data
US 2017/0055672 A1 Mar. 2, 2017

(30) Foreign Application Priority Data

May 7, 2014 (FR) ...................................... 14 54114

(51) Int. Cl.
*A45D 34/04* (2006.01)
*B05B 11/00* (2006.01)
(Continued)

(52) U.S. Cl.
CPC .............. *A45D 34/04* (2013.01); *A45D 34/00* (2013.01); *A61M 35/003* (2013.01);
(Continued)

(58) Field of Classification Search
CPC .. A45D 34/04; A45D 34/00; A45D 2034/005; A45D 2200/056;
(Continued)

(56) References Cited

U.S. PATENT DOCUMENTS 7,226,231 B2 * 6/2007 Py ........................ B65D 35/28
401/11
7,665,923 B2 * 2/2010 Py ........................ A45D 34/04
401/188 R
(Continued)

FOREIGN PATENT DOCUMENTS

GB  2 449 141 A  11/2008
WO  2013/121145 A1  8/2013

OTHER PUBLICATIONS

International Preliminary Report on Patentability and Written Opinion dated Nov. 17, 2016 from the International Bureau in counterpart International Application No. PCT/FR2015/051185.
(Continued)

*Primary Examiner* — David Walczak
(74) *Attorney, Agent, or Firm* — Sughrue Mion, PLLC

(57) ABSTRACT

A fluid dispenser and applicator assembly having a reception body, a fluid applicator surface for coming into contact with a target, such as the skin; and a fluid dispenser having a reservoir, a pump, and a dispenser endpiece that defines an outlet surface and a fluid dispenser orifice. The dispenser is received in the reception body with its dispenser endpiece being received in a housing, its outlet surface forming a portion of the applicator surface, such that the dispenser orifice opens out directly in the applicator surface.

12 Claims, 3 Drawing Sheets

(51) Int. Cl.
*A45D 34/00* (2006.01)
*A61M 35/00* (2006.01)
*B05B 15/00* (2018.01)

(52) U.S. Cl.
CPC ...... *B05B 11/0054* (2013.01); *B05B 11/3032* (2013.01); *A45D 2034/005* (2013.01); *A45D 2200/056* (2013.01); *A45D 2200/20* (2013.01); *A45D 2200/205* (2013.01); *A45D 2200/207* (2013.01); *B05B 11/0035* (2013.01); *B05B 11/00416* (2018.08); *B05B 15/00* (2013.01)

(58) Field of Classification Search
CPC ........ A45D 2200/205; A45D 2200/207; A45D 2200/20; A61M 35/003; B05B 11/0054; B05B 11/3032; B05B 11/0035; B05B 15/00; B05B 11/00416
See application file for complete search history.

(56) References Cited

U.S. PATENT DOCUMENTS

| | | | |
|---|---|---|---|
| 2011/0190672 A1 | 8/2011 | Apodaca et al. | |
| 2014/0234010 A1* | 8/2014 | Thorpe | A45D 34/04 401/265 |
| 2015/0232586 A1* | 8/2015 | Chen | C08F 10/02 525/293 |

OTHER PUBLICATIONS

International Search Report of PCT/FR2015/051185 dated Sep. 30, 2015 [PCT/ISA/210].

\* cited by examiner

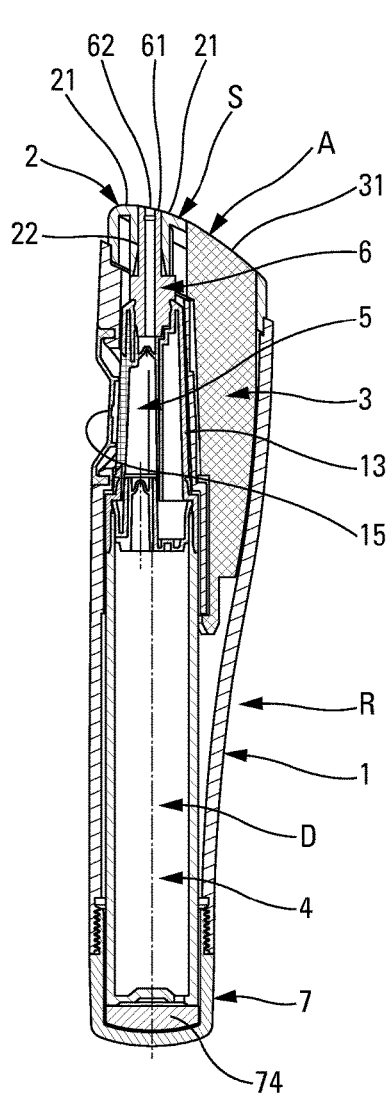
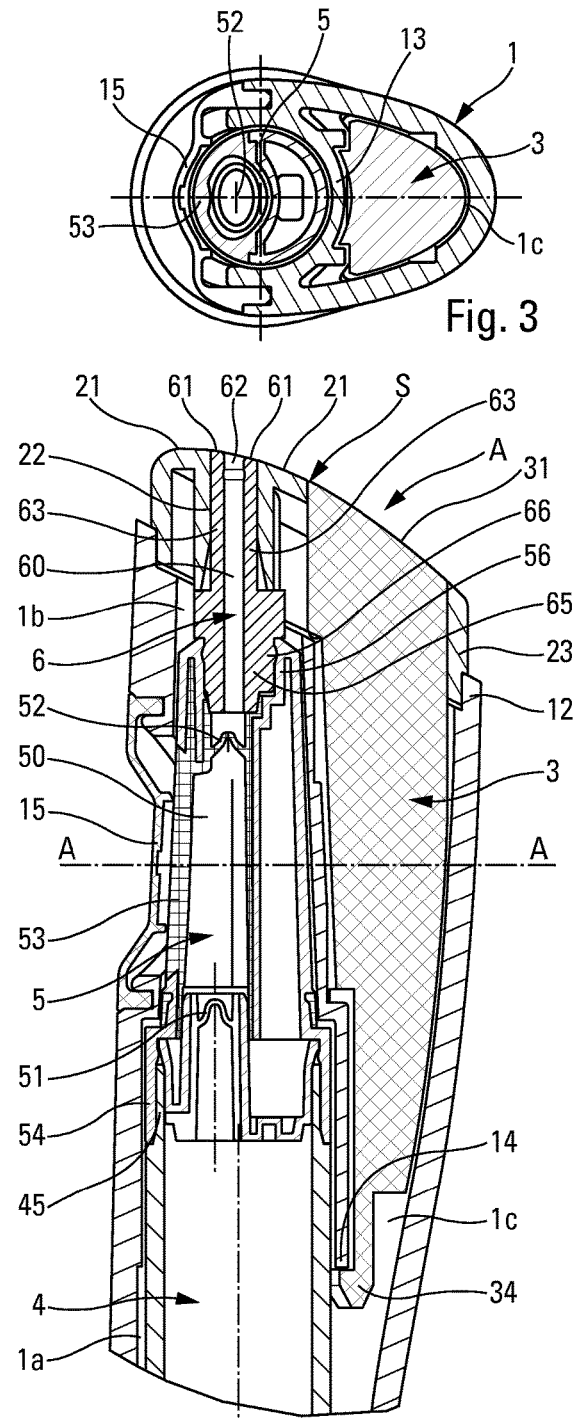
Fig. 1
Fig. 3
Fig. 2

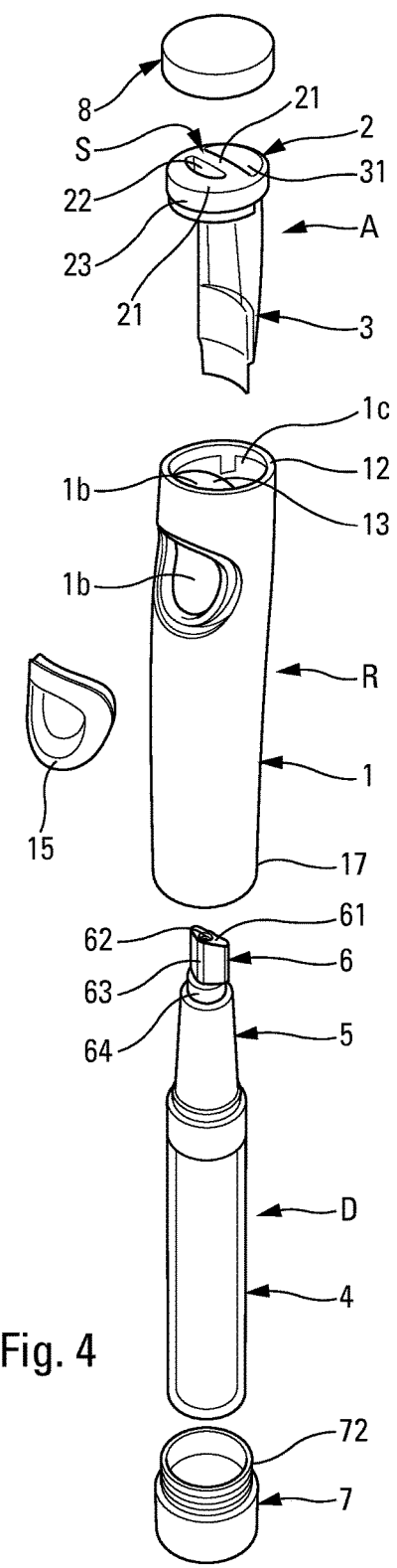
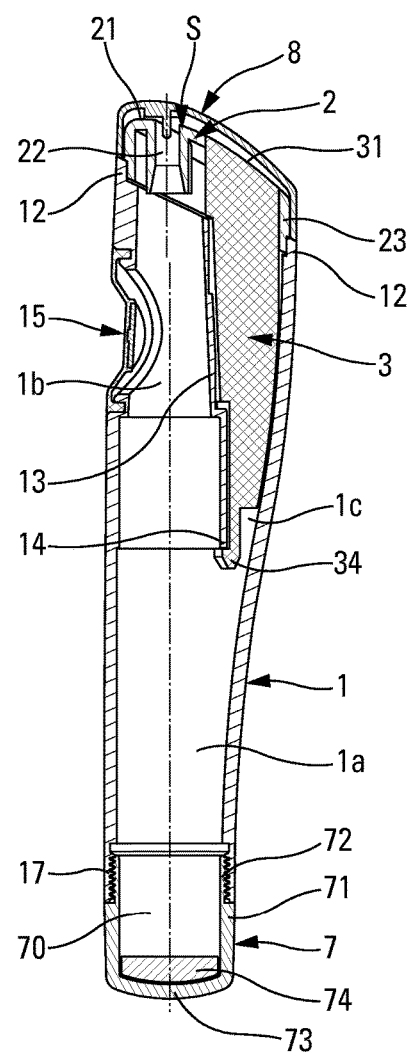
Fig. 4
Fig. 5

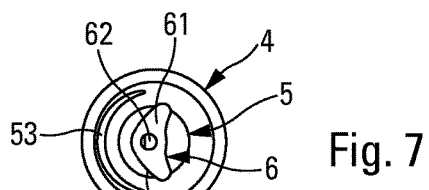
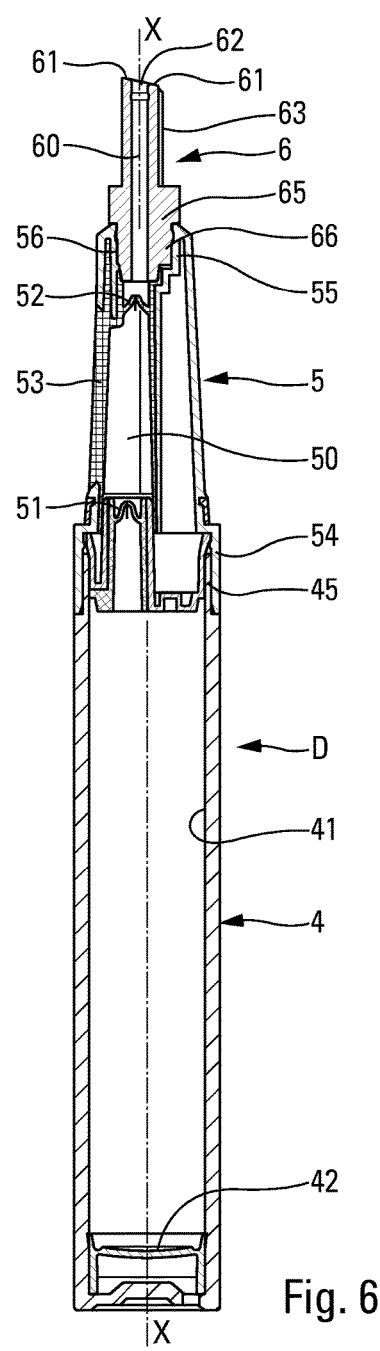
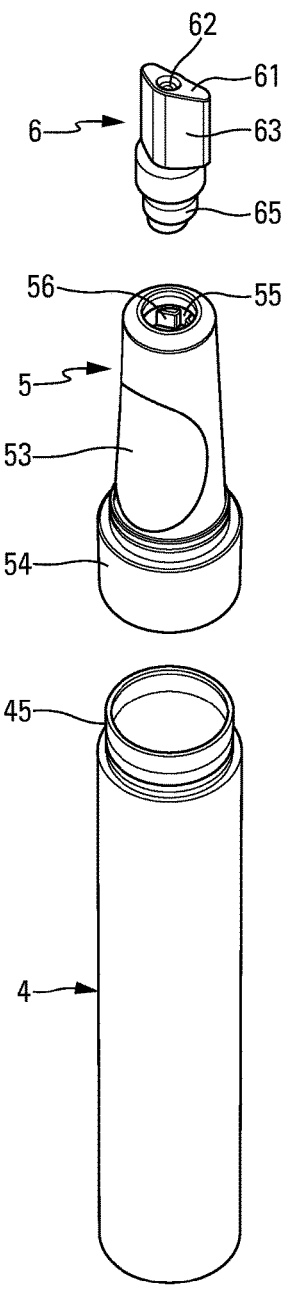

ASSEMBLY FOR DISPENSING AND APPLYING A FLUID PRODUCT

CROSS REFERENCE TO RELATED APPLICATIONS

This application is a National Stage of International Application No. PCT/FR2015/051185, filed May 5, 2015, claiming priority based on French Patent Application No. 1 454 114, filed May 7, 2014, the contents of all of which are incorporated herein by reference in their entirety.

The present invention relates to a fluid dispenser and applicator assembly comprising: a hollow reception body; a fluid applicator surface that is mounted at a top end of the reception body and that is for coming into contact with a target, such as the skin; and a fluid dispenser comprising a reservoir, a pump, and a dispenser endpiece that defines an outlet surface in which a fluid dispenser orifice opens out. The assembly advantageously includes a wave-generator module that emits waves and transmits them to the applicator surface. Thus, the assembly makes it possible to apply a fluid to a target such as the skin, and to subject the skin to waves through the applicator surface either simultaneously, subsequently, or previously. Naturally, an advantageous field of application for the present invention is the field of cosmetics, but it may also be the field of pharmacy.

In the prior art, document WO 2013/121145 is already known, which describes a dispenser and applicator assembly of this type. It comprises an applicator head that defines the applicator surface in which there opens out an outlet duct that forms a dispenser orifice. Furthermore, the applicator head includes a housing for a light source (LED) that emits red light having a wavelength of about 660 µm. The dispenser assembly includes a reception body in which a pump is incorporated. Furthermore, the body forms a housing for receiving the module that generates the red light. In its bottom portion, the assembly of that document includes a removable casing in which there is received a fluid reservoir that is mounted in removable manner on the pump that is incorporated in the body. The only removable and replaceable portion of the assembly is the fluid reservoir that is received in its casing. It is not possible to remove the pump from the body, given that the pump is molded directly inside the body. In addition, the applicator surface is formed solely and entirely by the head that forms the outlet duct and the dispenser orifice, and the reception housing for the light source.

Document US2011/0190672 is also known, which describes a vibrator applicator comprising a casing containing a reservoir that is provided with a dispenser endpiece. A collar arranged on the casing contains a vibrator element that surrounds the dispenser endpiece. A thermal storage head is coupled to the vibrator element so as to cause it to vibrate: the head is movable relative to the casing. The head defines an applicator surface in which the dispenser endpiece opens out. The collar includes a lateral pusher for actuating the vibrator element. The fluid is dispensed by squeezing the reservoir: a variant with a pump is described without going into detail. The dispenser is not intended to be disassembled and thus constitutes a unitary assembly.

An object of the present invention is to improve the fluid dispenser and applicator assemblies of the prior art by making them simultaneously more modular, cleaner, cheaper, and more easily adaptable to various wave-generating technologies.

To do this, the present invention proposes a fluid dispenser and applicator assembly comprising: a hollow reception body; a fluid applicator surface that is mounted at a top end of the reception body and that is for coming into contact with a target, such as the skin; and a fluid dispenser comprising a reservoir, a pump, and a dispenser endpiece that defines an outlet surface in which a fluid dispenser orifice opens out; the assembly being characterized in that the dispenser is received in removable manner in the reception body with its dispenser endpiece being received in removable manner in a housing, its outlet surface forming a portion of the applicator surface, such that the dispenser orifice opens out directly in the applicator surface, the dispenser being removable from the reception body through an open bottom end of the reception body, which bottom end is remote from the top end.

Thus, the fluid flows only inside the dispenser until it reaches the applicator surface, the outlet surface of which also forms a portion of the applicator surface. As a result, the fluid is in contact only with the dispenser and the applicator surface, to the exclusion of any other surface element. This does not apply to the dispenser assembly of document WO 2013/121145, in which the fluid on leaving the pump passes through a section of the reception body and the outlet duct formed by the applicator head. With the design of the invention, the dispenser and applicator assembly is much cleaner and much easier to clean. In the present invention, the entire dispenser comprising the reservoir, the pump, and the dispenser endpiece is received in removable manner in the reception body and in the housing. Thus, it is easy to remove a dispenser from the body and to replace it with another without any trace of fluid remaining inside the dispenser assembly. Specifically, this is possible given that the fluid flows only inside the dispenser until it reaches the applicator surface, as already mentioned above. Consequently, with a single dispenser and applicator assembly of the present invention, several types of fluid can be dispensed merely by replacing the fluid dispenser, and this without any risk of fluid remaining or of fluids becoming mixed together. It suffices for the user to clean the applicator surface properly before removing the fluid dispenser in order to insert another therein.

In another advantageous aspect of the invention, the dispenser endpiece and the housing present a corresponding cross-section imposing mutual engagement with a single angular orientation. Advantageously, the dispenser defines a longitudinal axis that passes via the reservoir, the pump, and the dispenser endpiece, the pump including a lateral actuator that is movable transversally relative to the longitudinal axis. Thus, the assembly may be gripped and handled like a pen by pressing on the lateral actuator by means of the index finger. Preferably, the dispenser endpiece has a particular orientation and is prevented from turning relative to the lateral actuator, the reception body including a lateral pusher that is arranged facing the lateral actuator so as to make it possible to move the lateral actuator by pressing laterally on the lateral pusher, the angular orientation of the dispenser in the reception body being imposed by the engagement of the dispenser endpiece in the housing.

In another very advantageous aspect of the invention, the applicator surface is formed, in part, by an applicator unit comprising an applicator head that forms the housing, and a wave-generator module that emits waves and transmits them to the applicator surface, the module being received, in part, in the reception body and advantageously forming a portion of the applicator surface. The waves emitted by the wave-generator module may be of any kind, e.g. visible light radiation; infrared or ultraviolet radiation; generally any kind of electromagnetic wave; or vibratory waves, e.g.

ultrasound; or mechanical waves (massage); etc. The wave-generator module may be associated with the applicator head by using any appropriate technique, e.g. by snap-fastening, adhesive bonding, force fitting, overmolding, adhesive bonding, etc.

Advantageously, the applicator unit is received in removable manner on and in the reception body, the module advantageously being snap-fastened in removable manner in the reception body. With such a design, it can easily be understood that the applicator unit is completely independent of the fluid dispenser, except for the engagement of the dispenser endpiece in removable manner inside the housing formed by the applicator head. It is thus possible to replace the applicator unit as a function of the fluid dispenser. It is thus possible to envisage providing several different types of fluid dispenser that are respectively associated different corresponding types of applicator unit including corresponding wave-generator modules.

According to a very practical characteristic of the invention, the outlet surface is arranged flush with the applicator surface so as to complete it in smooth, regular, and continuous manner. Advantageously, the outlet surface presents an outline having a shape that corresponds to the shape of the housing at least at the applicator surface, such that the dispenser endpiece closes the housing in sealed manner, at least at the applicator surface. It is thus guaranteed that the outlet surface is perfectly incorporated with the applicator surface without any possibility of fluid infiltrating into the housing. As a result, merely by cleaning the applicator surface quite simply, e.g. by rubbing or wiping, it is possible to remove the fluid dispenser from the assembly without any trace of fluid remaining in the reception body, the housing, or on the applicator surface.

In another advantageous aspect of the present invention, the assembly may include a removable bottom wall that co-operates with the reception body so as to close the bottom end, the removable bottom wall acting, advantageously in resilient manner, to push the dispenser towards the applicator head so as to press the dispenser endpiece into the housing. Preferably, the reservoir penetrates into the removable bottom wall so that the reservoir projects out from the reception body after the bottom wall has been removed, enabling the reservoir to be gripped and enabling the dispenser to be removed from the reception body. Not only is it guaranteed that the dispenser endpiece is sealed in the housing, but it is also guaranteed that the dispenser is held inside the reception body in stable manner, while enabling it to be removed easily.

In another advantageous approach of the invention, it should be observed that the assembly comprises three distinct units that are assembled together in removable manner, namely: a reception unit that is formed by the reception body and that is advantageously provided with a pusher and with a removable bottom wall; an applicator unit that forms the applicator surface and that comprises an applicator head and a wave-generator module; and a dispenser unit that is constituted by the fluid dispenser. It can be seen at once that the assembly is the result of assembling together three distinct units that provide simultaneously modularity, easy cleaning, and easy assembly, and as a result that provide low cost of manufacturing the assembly. Advantageously, the pump is arranged between the pusher and the module. As a result of this compact design, the assembly may be in the form of a pen with a rounded portion in which the pump, the pusher, and the module are all arranged.

The spirit of the invention resides in the fluid leaving the dispenser only at the applicator surface, and this is even more advantageous when the dispenser is mounted in removable manner and when the applicator surface is formed, at least in part, by an applicator unit that also incorporates a wave-generator module. Separating the assembly into three distinct units is also an advantageous characteristic, since it makes it possible to disassociate the dispenser from the wave-generator module, which may thus be designed and manufactured by different suppliers.

The invention is described below in greater detail with reference to the accompanying drawings, which show an embodiment of the invention by way of non-limiting example.

In the figures:

FIG. 1 is a substantially life-size vertical-section view through a fluid dispenser and applicator assembly of the invention;

FIG. 2 is a greatly enlarged view of the top portion of FIG. 1;

FIG. 3 is a horizontal cross-section view on section line A-A in FIG. 2;

FIG. 4 is an exploded perspective view of the dispenser and applicator assembly in the above figures;

FIG. 5 is a view similar to the view in FIG. 1, in the absence of a fluid dispenser;

FIG. 6 is a vertical section view through a fluid dispenser of the invention;

FIG. 7 is a plan view of the FIG. 6 dispenser; and

FIG. 8 is an exploded perspective view of the dispenser in FIGS. 6 and 7.

As can be seen from the various figures which illustrate the present invention, the fluid dispenser and applicator assembly of the invention presents an elongate or slender shape that may be similar to the shape of a pen. It should also be observed that its cross-section is not constant, since it varies significantly from bottom to top. Specifically, in the proximity of its bottom end, the dispenser and applicator assembly presents a cross-section that is generally round or circular, while at the section line A-A, which is generally situated in the proximity of the top end, the dispenser and applicator assembly presents a cross-section that is egg shaped (FIG. 3). The top face of the assembly forms an applicator surface S that inclines or slopes towards one side.

With reference to FIG. 4, it is possible to see the various component elements of the dispenser and applicator assembly of the invention. Initially, it should be observed that it comprises three main distinct units, namely a dispenser unit D, a reception unit R, and an applicator unit A. The dispenser unit D, which is a fluid dispenser, is advantageously received in removable manner inside the reception unit R that comprises a single-piece reception body 1 having an inside that is hollow. The applicator unit A is mounted on and in the body 1, advantageously in removable manner. Thus, the two units D and A are preferably received in removable manner on and in the body 1 from the two opposite ends 17 and 12 respectively. This is the general structure of the dispenser and applicator assembly of the invention.

In greater detail, the body 1 of the reception unit R is open at its top and bottom ends 12, 17 so as to be able to receive the units A and D. The inside of the bottom end 17 is advantageously threaded so as to receive a removable bottom wall 7 by screw-fastening. The removable bottom wall presents the shape of a small pot with a bottom wall 73 and a cylindrical side wall 71 having a top portion that forms a thread 72 having a pitch that corresponds to the pitch of the bottom end 17 of the body 1. It should be observed that on top of its bottom wall 73, the removable bottom wall 7 is provided with a piece of elastic material 74 that may be foam or an elastomer. The inside of the removable bottom wall 7 forms a space 70 that upwardly communicates with the inside of the body 1, which itself defines a reception space 1a. Beyond the reception space 1a, the inside of the body 1 is divided into two compartments 1b and 1c by a separating partition 13. The compartment 1b extends axially running on from the space 1a, while the compartment 1c extends laterally, where the body 1 defines its egg shape. The bottom end of the partition 13 forms a snap-fastener edge 14, as described below. Level with the compartment 1b, the body 1 is provided with a lateral pusher 15 that is movable transversally relative to the longitudinal axis of the reception body 1. The pusher 15 may be moved purely in translation or it may be deformed elastically. By way of example, it is possible to envisage molding the pusher 15 onto the reception body 1, using an elastomeric material. In a variant, it is also possible to envisage a pusher 15 that moves completely independently of the body 1. It is also possible to envisage not having a pusher 15 but only an opening. It should also be observed that the separator partition 13 extends into the proximity of the top end 12. The reception body 1 may be made merely by injection molding plastics material, or it may even be made of metal.

In this embodiment, the applicator unit A results from combining an applicator head 2 and a wave-generator module 3. As can be seen in FIGS. 1 and 2, the applicator head 2 includes an axial housing 22 that is formed by a cylindrical tube having a cross-section that presents a geometrical shape that is complex, e.g. the shape of a crescent. The housing 22 is upwardly connected to an applicator-surface area 21 that, in this embodiment, is formed with two openings, namely a first opening corresponding to the mouth of the housing 22, and a second opening for the module 3. More precisely, the module 3 includes an applicator-surface section 31 that closes the corresponding opening of the head 2 in such a manner as to complete the applicator-surface area 21 of the head 2 in continuous and smooth manner. In other words, the module 3 fits in the opening of the applicator head, so that the applicator-surface section 31 of the module 3 finishes off the applicator-surface area of the head 2 without creating any projecting or recessed discontinuities. Consequently, assembling the module 3 and the head 2 together makes it possible to create an applicator surface S having a single opening that, at this stage, is formed by the mouth of the housing 22. In FIGS. 1 and 2, it should be observed that the applicator-surface section 31 occupies the portion of the applicator surface S that slopes the most. The applicator head 2 also includes a peripheral skirt 23 that fits in the top end 12 of the hollow body 1. In addition, the wave-generator module 3 extends inside the reception space 1c, and advantageously presents a snap-fastener profile 34 that is suitable for co-operating with the bottom edge 14 of the separator partition 13. In this way, the applicator unit A may be mounted in completely stable manner on and in the hollow body 1.

In the invention, the wave-generator module 3 makes it possible to generate any type of electromagnetic, vibratory, etc. wave or radiation, e.g. visible, infrared, or ultraviolet light, or microwaves, etc., or even ultrasound, or mechanical vibration. The module 3 may also generate heat or cold (thermal waves) so as to impart a hot or cold effect on contact with the skin.

The dispenser unit or fluid dispenser D comprises a fluid reservoir 4, a pump 5, and a dispenser endpiece 6, as can be seen more clearly in FIGS. 6 to 8.

By way of example, the reservoir 4 may be in the form of a slide cylinder 41 in which there is received a follower piston 42 that is adapted to slide in the cylinder 41 as the fluid is extracted from the reservoir. The top of the cylinder 41 forms a neck 45. Instead of this particular reservoir, it is also possible to envisage a simpler reservoir in which the working volume does not vary, or a reservoir with a flexible pouch.

The pump 5 includes a fastener ring 54 that enables it to be mounted on the neck 45 of the reservoir 4. The pump 5 includes a pump chamber 50 that, at its bottom end, is provided with an inlet valve 51, e.g. in the form of a slotted shutter. At its top end, the pump chamber 50 includes an outlet valve 52 that may also be made in the form of a slotted shutter, for example. Furthermore, the pump chamber 50 includes a lateral actuator 53 that makes it possible to reduce the working volume of the pump chamber 50, and thus force the fluid through the outlet valve 52. The lateral actuator 53 is movable perpendicularly to the longitudinal axis X of the dispenser D. The movement may be in translation or by elastic deformation. In the embodiment used to illustrate the present invention, the actuator 53 is in the form of a flexible wall of the pump chamber 50 that is made by a method of bi-injection or of overmolding, for example. The pump 5 may thus be referred to as a flexible-diaphragm pump, in the sense that a movable wall of the chamber is actuated directly in order to put the fluid under pressure. At its top end, the pump 5 forms a mounting well 56 for mounting the dispenser endpiece 6. The mounting well 56 is advantageously provided with keying means 55, e.g. in the form of a projecting profile or a recess, making it possible to impose the angular orientation of the endpiece 6 in the well 56.

The dispenser endpiece 6 thus includes a mounting stub 65 that is engaged, and advantageously snap-fastened, inside the mounting well 56. The mounting stub 65 includes a keying profile that fits perfectly in the keying means 55 of the well 56, so as to impose the angular orientation of the dispenser endpiece 6 on the pump 5. In this way, the endpiece is always oriented in the same way relative to the lateral actuator 53 that extends on one side only of the pump 5. Above the mounting stub 65, the dispenser endpiece 6 forms an insertion appendage 63 having a cross-section that presents a shape that corresponds to the shape of the housing 22 formed by the applicator head 2. This shape can be seen more clearly in FIG. 7: it is similar to the shape of a crescent. The side wall of the insertion appendage 63 may be a non-circular cylinder over its entire height. In a variant, one or more projecting sealing beads may be provided, making it possible to establish sealing inside the housing 22. At its top end, the appendage 63 forms a substantially-plane outlet surface 61 that is perforated with a dispenser orifice 62, forming the outlet of an outlet duct 60 that passes through the appendage 63 and the mounting stub 65, as can be seen clearly in FIGS. 2 and 6.

Once the dispenser endpiece 6 is mounted on the pump 5, as visible in FIG. 6, it can be seen that the outlet valve 52 communicates directly with the outlet duct 60. Thus, by depressing the lateral actuator 53, the working volume of the pump chamber 50 is reduced, and fluid under pressure is forced through the outlet valve 52, from where it can flow through the outlet duct 60 until it reaches the dispenser orifice 62 situated at the outlet surface 61. When the pressure on the lateral actuator 53 is relaxed, the outlet valve 52 closes and the inlet valve 51 opens under the effect of the suction created in the pump chamber 50, thus enabling fluid to be sucked up from the reservoir 4, in which the follower piston 42 then moves towards the pump 5.

As can be understood from FIG. 4, the dispenser unit of the dispenser D is inserted inside the hollow body 1 through its bottom end 17, after removing the removable bottom wall 7. The dispenser D is thus inserted axially through the space 1a, then through the space 1b until the dispenser endpiece 6 penetrates into the housing 22 of the applicator head 2. As explained above, it is necessary to orientate the dispenser D angularly, so that its insertion appendage 63 is engaged inside the housing 22. The angular orientation is preferably a single angular orientation. It is thus possible to engage the appendage 63 fully inside the housing 22 until the outlet surface 61 comes level with the applicator surface S so as to finish it off. This can be seen in FIG. 2. It can be seen that the outlet surface 61 becomes completely flush with the applicator-surface area 21 of the head 2 so as to finish it off. Finally, only the dispenser orifice 62 breaks the continuity of the applicator surface S. In order to guarantee that the appendage 63 is engaged fully in the housing 22, use is made of the removable bottom wall 7 having flexible material 74 that comes into contact with the bottom wall of the reservoir 4 so as to push it upwards, and establish sealing at the housing 22. In this respect, it should also be observed that the bottom end of the reservoir 4 projects out from the hollow body 1 when the removable bottom wall 7 is removed, so as to make it easy to grip the dispenser by its reservoir 4 in order to remove it from the hollow body 1. As a result, the dispenser D is received in removable manner inside the hollow body 1 and the head 2. It should also be observed that the imposed angular orientation of the appendage 63 inside the housing 22 makes it possible to arrange the lateral actuator 53 facing the pusher 15 of the hollow body 1.

FIG. 3 shows the arrangement of the various component elements of the dispenser and applicator assembly of the invention, where it presents its egg shape. By way of example, it is possible to see that the generator module 3 is received inside the compartment 1c that is defined by the separator partition 13 that surrounds, in part, the pump 5, having its lateral actuator 53 covered by the lateral pusher 15. It can thus be said that the pump 5 is arranged between the module 3 and the pusher 15, inside the hollow body 1.

With such a design, the applicator unit A is received in removable manner on and in the reception unit R. In addition, the dispenser unit of the dispenser D is also received in removable manner inside the reception unit R and inside the housing 22 of the applicator unit A. In this way, the dispenser D and the applicator unit A may be replaced at will as a function of requirements. By way of example, it is possible to envisage that a particular dispenser dispensing a particular fluid is associated with a particular applicator unit. It thus suffices to mount the two units A and D in the reception unit R in order to constitute the dispenser and applicator assembly of the invention. When it is necessary to replace the units A and D, it is possible to remove each of them easily from the reception unit R.

It should also be observed that the fluid dispensed by the dispenser D leaves the dispenser only at the applicator surface S, such that no fluid can remain inside the reception unit R once the dispenser has been removed. Furthermore, as a result of the applicator surface S being completely smooth and continuous, it can easily be cleaned by rubbing or wiping. Thus, when a user wishes to change a dispenser, it suffices for the user to clean the applicator surface S beforehand, then to remove the dispenser and replace it with another. No soiling or fluid deposit can be observed.

In the embodiment used to illustrate the present invention, the wave-generator module 3 forms an applicator-surface sector 31. This is a particular non-limiting embodiment only, since it is entirely possible to envisage making the wave-generator module 3 without it forming a portion of the applicator surface S. By way of example, the module 3 may be associated with the applicator head 2 just below the applicator surface S, which applicator surface thus serves as diffuser means for diffusing the waves.

The complete independence between the dispenser D and the applicator unit A, except when assembled in the housing 22, makes it possible to disassociate the two units completely, such that they may be produced by entirely different suppliers, namely a supplier specialized in the design of dispensers, and a supplier specialized in the design of electronic wave-generator modules.

By means of the invention, a fluid dispenser and applicator assembly is obtained comprising three distinct units for which cleanliness and cleaning are easily guaranteed.

The invention claimed is:

1. A fluid dispenser and applicator assembly comprising:
a hollow reception body;
a fluid applicator surface that is mounted at a top end of the reception body and that is for coming into contact with a target, such as the skin; and
a fluid dispenser comprising a reservoir, a pump, and a dispenser endpiece that defines an outlet surface in which a fluid dispenser orifice opens out;
the assembly being characterized in that the dispenser is received in removable manner in the reception body with its dispenser endpiece being received in removable manner in a housing, its outlet surface forming a portion of the applicator surface, such that the dispenser orifice opens out directly in the applicator surface, the dispenser being removable from the reception body through an open bottom end of the reception body, which bottom end is remote from the top end.

2. An assembly according to claim 1, wherein the dispenser endpiece and the housing present a corresponding cross-section imposing mutual engagement with a single angular orientation.

3. An assembly according to claim 1, wherein the dispenser defines a longitudinal axis X that passes via the reservoir, the pump, and the dispenser endpiece, the pump including a lateral actuator that is movable transversally relative to the longitudinal axis X.

4. An assembly according to claim 3, wherein the dispenser endpiece has a particular orientation and is prevented from turning relative to the lateral actuator, the reception body including a lateral pusher that is arranged facing the lateral actuator so as to make it possible to move the lateral actuator by pressing laterally on the lateral pusher, the angular orientation of the dispenser in the reception body being imposed by the engagement of the dispenser endpiece in the housing.

5. An assembly according to claim 1, wherein the outlet surface presents an outline having a shape that corresponds to the shape of the housing at least at the applicator surface, such that the dispenser endpiece closes the housing in sealed manner, at least at the applicator surface.

6. An assembly according to claim 1, wherein the applicator surface is formed, in part, by an applicator unit comprising an applicator head that forms the housing, and a wave-generator module that emits waves and transmits them to the applicator surface, the module being received, in part, in the reception body and advantageously forming a portion of the applicator surface.

7. An assembly according to claim 6, including a removable bottom wall that co-operates with the reception body so as to close the bottom end, the removable bottom wall acting, advantageously in resilient manner, to push the dispenser towards the applicator head so as to press the dispenser endpiece into the housing.

8. An assembly according to claim 7, wherein the reservoir penetrates into the removable bottom wall so that the reservoir projects out from the reception body after the removable bottom wall has been removed, enabling the reservoir to be gripped and enabling the dispenser to be removed from the reception body.

9. An assembly according to claim 6, wherein the applicator unit is received in removable manner on and in the reception body, the module advantageously being snap-fastened in removable manner in the reception body.

10. An assembly according to claim 1, wherein the outlet surface is arranged flush with the applicator surface so as to complete it in smooth, regular, and continuous manner.

11. An assembly according to claim 1, comprising three distinct units that are assembled together in removable manner, namely:
  a reception unit that is formed by the reception body and that is advantageously provided with a pusher and with a removable bottom wall;
  an applicator unit that forms the applicator surface and that comprises an applicator head and a wave-generator module; and
  a dispenser unit that is constituted by the fluid dispenser.

12. An assembly according to claim 11, wherein the pump is arranged between the pusher and the wave-generator module.

* * * * *